United States Patent
Kaito

(10) Patent No.: US 7,550,723 B2
(45) Date of Patent: Jun. 23, 2009

(54) ATOM PROBE APPARATUS AND METHOD FOR WORKING SAMPLE PRELIMINARY FOR THE SAME

(75) Inventor: Takashi Kaito, Chiba (JP)

(73) Assignee: SII NanoTechnology Inc. (JP)

( * ) Notice: Subject to any disclaimer, the term of this patent is extended or adjusted under 35 U.S.C. 154(b) by 261 days.

(21) Appl. No.: 10/592,844

(22) PCT Filed: Mar. 2, 2005

(86) PCT No.: PCT/JP2005/003495

§ 371 (c)(1),
(2), (4) Date: Nov. 20, 2006

(87) PCT Pub. No.: WO2005/090941

PCT Pub. Date: Sep. 29, 2005

(65) Prior Publication Data

US 2007/0176099 A1    Aug. 2, 2007

(30) Foreign Application Priority Data

Mar. 17, 2004    (JP) .............................. 2004-075873

(51) Int. Cl.
G01N 31/00 (2006.01)
G01N 23/00 (2006.01)
G01N 33/00 (2006.01)
G21K 7/00 (2006.01)
G21K 5/10 (2006.01)
H01J 37/08 (2006.01)
G01F 23/00 (2006.01)

(52) U.S. Cl. ...................... 250/306; 250/304; 250/307; 250/309; 250/492.21; 250/440.11

(58) Field of Classification Search ................. 250/304, 250/306, 307, 309, 492.21, 440.11; 977/840, 977/849, 858, 864, 890
See application file for complete search history.

(56) References Cited

U.S. PATENT DOCUMENTS 6,875,981 B2 * 4/2005 Nishikawa .................. 250/306
2003/0066962 A1 * 4/2003 Kaito et al. .................. 250/306
2004/0056195 A1 * 3/2004 Kuhlman et al. ............ 250/307

FOREIGN PATENT DOCUMENTS

JP        2001208659 A  *  8/2001

* cited by examiner

Primary Examiner—Jack I Berman
Assistant Examiner—Brooke Purinton
(74) Attorney, Agent, or Firm—Adams & Wilks

(57) ABSTRACT

A preliminary processing technology for a sample locally cuts out a sample part of a device to be analyzed and processes it into a needle-like projection, and a technology of realizing SAP analysis on an atomic level by ensuring stabilized ion evaporation sequentially even in the case of a sample of multilayer structure including an element layer of small evaporation electric field. The preliminary processing method for a sample used on atom probe apparatus comprises a step for cutting the desired observing part of the sample into a block using an FIB equipment, a step for transferring the sample block onto a sample substrate and fixing the sample block in place, and a step for processing the sample block fixed onto the sample substrate into a needle-point shape by FIB etching. The sample processed into a needle-point shape is shaped such that the layer direction of the multilayer structure becomes parallel to the longitudinal direction of the needle.

11 Claims, 3 Drawing Sheets

ATOM PROBE APPARATUS AND METHOD FOR WORKING SAMPLE PRELIMINARY FOR THE SAME

CROSS-REFERENCE TO RELATED APPPLICATIONS

This application is a U.S. national stage application of International Application No. PCT/JP2005/003495, filed Mar. 2, 2005, claiming a priority date of Mar. 17, 2004, and published in non-English language.

TECHNICAL FIELD

The present invention relates to a sample arrangement in an atom probe apparatus possessing a hollow conical ion lead-out electrode, and a method for working an acicular sample preliminarily.

BACKGROUND ART

As shown in FIG. 3, the first high resolution microscope utilizing a tunnel phenomenon of electrons has been a field emission microscope FEM (Field Emission Microscope) in which electrons are radiated from a sharp needle tip, and the electrons produce a radiated electron image of the needle tip projected while being enlarged. This microscope is one utilizing an electric field radiation phenomenon in which, if a strong electric field is applied under a vacuum state, the electrons are emitted from a metallic conductor surface beyond a barrier of a surface potential by a quantum-mechanical tunnel effect, and is such that, by being so constituted that an electron radiation is performed from a tip surface of the metal formed like the needle toward a screen coated with a fluorescent material by an action of strong electric field, there is depicted the enlarged image of an emitted metal surface onto the fluorescent screen.

Although the atom cannot be seen because the resolution of the FEM is as low as about 1 nm, there is found a work function of a fine crystalline face on a semispherical face of the needle tip from an I-V characteristic of a negative voltage applied to the needle and a radiation current. If the applied voltage is switched from negative to positive and an inert gas of low pressure is introduced into a microscope body, the FEM operates as a field ion microscope FIM (Field Ion microscope) and it becomes possible to directly observe an atomic arrangement of the needle tip. The FIM has a characteristic capable of desorbing the surface atom of the needle tip in correct order as a positive ion by an electric field evaporation phenomenon. This phenomenon is utilized also in an atomic operation by a scanning tunneling microscope STM (Scanning Tunneling Microscope). If the desorbed ions are detected and identified one by one, a composition of the needle tip can be analyzed at an atomic level. On the bases of this concept, there has been developed a composite atom probe AP (Atom Probe) of a mass spectrometer capable of detecting a single ion and the FIM. The AP is the only apparatus capable of analyzing an electron state, an atomic arrangement and a composition distribution of the needle tip. Since the electric field evaporation advances in correct order in every atom layer from a surface first layer, by the AP it is possible to investigate a composition of every layer, a composition distribution of an interface and, in addition, an electron state change.

However, in this AP there is a strict restriction in a manufacture and shape of a sample, and a field capable of making the best use of its characteristic has been limited. It is a scanning atom probe (SAP: Scanning Atom Probe) that has been devised in order to break down this restriction. In order to select a specific needle from closely arranged needles and investigate its tip, an electric field must be localized to the needle tip. Whereupon, a grounded lead-out electrode of a fine funnel type is attached to an inside of the microscope body of the AP, and a positive voltage is applied to the planar sample in which the fine needles are closely arranged. Then, a high electric field is generated in a single needle tip existing just below a hole at the tip of lead-out electrode whose diameter is several μm to several tens μm, and the electric field is localized to a very narrow space between the hole and the needle tip. According to an electric field distribution calculation by a computer, even in a case where an apex angle of the needle tip is 90° and a radius of curvature of the tip is 50 nm, in the needle tip there is generated a high electric field demanded for the electric field radiation and the electric field evaporation. This fact shows the fact that, if there are irregularities of about several μm on the flat sample face, a tip of its protrusion can be analyzed. Since a surface to which no smoothing treatment has been applied, a corroded surface, a surface of a high efficiency catalyst, and the like are generally rich in their irregularities, it follows that these surfaces are investigated as they are. A basic structure of the SAP is shown in FIG. 4. The sample in a left end schematically shows a closely arranged type electric field radiation electron source. If the hole in the tip of the funnel type lead-out electrode approaches the needle tip on the sample face or a tip of the protrusion, the high electric field is generated in a very narrow region between the tip and the electrode, and the electrons radiated from the needle tip depict an FEM image on the screen. Further, if an inert image gas such as helium is introduced into the microscope body and the positive voltage is applied to the sample, a high resolution FIM image is depicted on the screen. Additionally, if the surface atoms are electric-field-evaporated by superposing a pulse voltage onto a steady-state voltage or irradiating a pulse laser light to the sample face, the surface atoms which have evaporated as positive ions pass through a survey hole in a screen center and enter into a refletron that is the mass spectrometer, and are detected one by one. The region to be analyzed is a region in which a diameter of its protrusion tip corresponding to the survey hole is several nano to several tens nano. If the analysis is continued, it is possible to investigate a composition change in a depth direction of this region by the resolution of one atom layer.

In this document, the sample in whose surface there exist the irregularities is made an analysis object, and there are shown the fact that, by finding out especially a convex portion and causing it to face the lead-out electrode, if the sample protrusion part is electric-field-evaporated in order from upper layer atoms to thereby draw out them as ions and they are detected by an ion detector (two-dimensional detection type) disposed behind the above lead-out electrode, an element analysis can be made by a time-of-flight measurement of each ion, and the fact that, since also a position information can be obtained, a three-dimensional composition analysis at the atomic level is possible.

On the other hand, in a case where the analysis object sample such as a semiconductor wafer for which there is a strong analysis need and a thin film magnetic head wafer called GMR or TMR is made the sample, it is frequent that the sample becomes a multilayer structure in which complicated patterns have been stacked, so that the structure of a portion that is desired to be analyzed varies. In order to analyze such an analysis object by using the AP, it is necessary to locally cut out a place that is desired to be analyzed to thereby cut out as a fine section in a tip of an acicular protrusion becoming the electrode in the tip and fix it. However, heretofore, there has existed only an old method of making the sample such as metal material acicular, and it has been very difficult to analyze a fine specified site by the AP. For this reason, as a method for this, it becomes indispensable to develop a preliminary working technique which works the sample itself into an acicular form. With a relation that it is the analysis at the atomic level, since an analysis object dimension becomes about 100 nm cubed, a technique for manufacturing at a pin point an analysis object part to an acicular sample becomes very important.

[Patent Document 1] Japanese Patent Application No. 2003-157120 Specification "Method of positioning a vertical position of a pickup sample and a sample having a mark showing a vertical direction"

[Non-Patent Document 1] By Morita Shozo "Scanning Probe Microscope: Base and Future Estimate", Published by Maruzen on Feb. 10, 2000, 2.7 Scanning Atom Probe (SAP), 70-73 pages

[Non-Patent Document 2] Edited and Written by Nishikawa Osamu "Scanning Probe Microscope: from STM to SPM" Published by Maruzen on Mar. 30, 1998, Description on 8 page, and Table 1-2 Evaporation electric field intensities of various elements

SUMMARY OF THE INVENTION

Problems that the present invention is to solve are to present a technique for preliminarily working a sample, which makes a place, that is desired to be analyzed, of a device into an acicular protrusion by locally cutting out the place without an SAP analysis object sample being limited to a protrusion part possessing the fine irregularities, and to provide, even if the sample is a sample of the multilayer structure containing element layers whose evaporation electric fields largely differ in later-mentioned circumstances, a technique for making a stable ion evaporation in order possible, thereby making an SAP analysis at the atomic level possible.

A preliminary working of a sample for an atom probe apparatus of the present invention comprises a step of cutting out a sample's desired observation site to a block-like form by using an FIB (Focused Ion Beam) apparatus, a step of carrying and fixing the block-like cut-out sample onto a fixing substrate, and a step of working the block-like sample fixed onto the fixing substrate into a needle tip shape by an FIB etching.

Further, a method of fixing the block-like cut-out Sample onto the sample substrate has a step of temporarily bonding it by an FIB-CVD (Focused Ion Beam-Chemical Vapor Deposition or Focused-Ion-Beam-Assisted Chemical Vapor Deposition), and a step of cutting in a groove over a base part of the block-like sample and the sample substrate by an FIB etching, and has been adapted such that thereafter the FIB-CVD is applied to the cut-in portion, thereby bonding and fixing the sample substrate and the block-like sample.

A method for working a sample preliminarily for an atom probe apparatus of the present invention has been adapted such that, in a finish working for working the block-like sample into the needle tip shape by the FIB etching working, it is performed by an acceleration voltage of 10 kV or lower, thereby shallowing a damage layer.

A method for working a sample preliminarily for an atom probe apparatus of the present invention has been adapted so as to go through a process of additionally removing, after performing the finish working by the acceleration voltage of 10 kV or lower, the damage layer by a low acceleration Ar ion milling and the like.

A sample for an atom probe apparatus of the present invention has been adapted such that the sample worked into a needle tip shape is formed such that a layer direction of a multilayer structure becomes parallel to a longitudinal direction of a needle.

An atom probe apparatus of the present invention has been adapted so as to possess a storage means in which there has been accumulated an information as to which layer of an element first electric-field-evaporates and the like, and means for detecting an arrival position to a screen becoming an ion detector.

Additionally, a sample for an atom probe apparatus of the present invention possesses a function of discriminating and analyzing different elements which ion-evaporate while being mixed, from an FIM image of a screen becoming an ion detector.

Since a method for working a sample preliminarily for an atom probe apparatus of the present invention is one comprising a step of cutting out a sample's desired observation site to a block-like form by using an FIB apparatus, a step of carrying and fixing the block-like cut-out sample onto a sample substrate, and a step of working the block-like sample fixed onto the sample substrate into a needle tip shape by an FIB etching, it is possible to cut out the sample's desired observation site to thereby form it into a sharp needle tip shape suitable as the sample for the atom probe apparatus.

Further, since the method for working a sample preliminarily for an atom probe apparatus of the present invention is one having, as a method of fixing the block-like cut-out sample onto the sample substrate, a step of temporarily bonding it by an FIB-CVD and a step of cutting in a groove over a base part of the block-like sample and the sample substrate by an FIB etching, and having been adapted such that thereafter the FIB-CVD is applied to the cut-in portion, it has been possible to firmly bond and fix the sample substrate and the block-like sample. By this, it is possible to stably perform a test by the atom probe apparatus.

In the finish working for working the block-like sample into the needle tip shape by the FIB etching working, by performing it by the acceleration voltage of 10 kV or lower, it is possible to suppress as much as possible a damage in which irradiated ions are left in the sample.

Further, after performing the finish working by the acceleration voltage of 10 kV or lower, it is possible to additionally remove that damage layer by the low acceleration Ar ion milling and the like.

Since the sample for an atom probe apparatus of the present invention worked into needle tip shape is formed such that the layer direction of the multilayer structure becomes parallel to the longitudinal direction of the needle, in the multilayer structure even if there exist layers of elements whose evaporation voltages are different, there is no fact that they exfoliate in their boundary face, so that it is possible to stably perform the test by the atom probe apparatus.

Since a sample for an atom probe apparatus of the present invention is one possessing the storage means in which there has been accumulated the information as to which layer of the element first evaporates and the like, and means for detecting the arrival position to the screen becoming the ion detector, on the basis of that information it is possible to index an end part position of the layer of an element to be specified.

An atom probe apparatus of the present invention has made it possible to respectively discriminate and analyze different elements which ion-evaporate while being mixed.

Figure 1A:
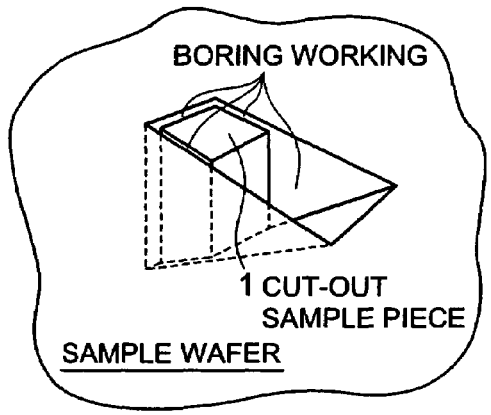
[FIG. 1]

It is a view explaining a method of the present invention, which preliminarily works an acicular sample for an SAP.

[FIG. 2]

It is a view explaining a method of the present invention, which makes a layer of a multilayer structure sample into an axial direction of a needle and thereby preliminarily works it to the acicular sample for the SAP.

[FIG. 3]

It is a view explaining a basic constitution of a field emission microscope FEM.

[FIG. 4]

It is a view showing and explaining a basic constitution canning atom probe SAP.

DESCRIPTION OF REFERENCE NUMERALS 1 cut-out sample piece
1a acicular sample
2 sample fixing substrate
3 probe
4, 4a, 4b protective film
5 temporarily fixing part
6 completely fixing part

DETAILED DESCRIPTION OF THE INVENTION

Figure 1B:
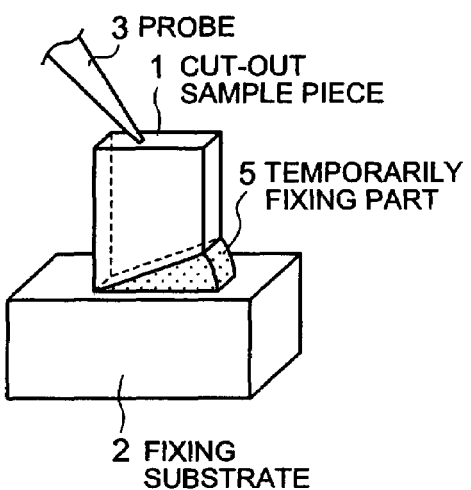

In order to perform, by the technique of the AP, the analysis of every atom layer of the device which becomes the multilayer structure in which the complicated patterns have been stacked, the present inventors have attempted a preliminary working of the sample and an analysis using the sample. First, as the preliminary working of the sample, there was adopted a working method in which a sample piece in the form of a sample block of the device was cut out by using a focused ion beam (FIB) apparatus, it was carried and fixed onto a sample substrate, and additionally it was finished to the acicular sample by using the FIB apparatus. In this procedure, by using a scanning ion microscope (SIM) function of the FIB apparatus, an observation-desired place of the device is specified from a wafer-like large sample for instance, and a protective film is formed on its surface by an FIB-CVD. Here, in a case where a region that is desired to be analyzed by the AP exists in the sample surface, a protective film is applied before an FIB irradiation in order to avoid a damage such as Ga ion implantation by the FIB irradiation. The protective film can be formed by a method using a vacuum evaporator or a sputter film-forming apparatus. Incidentally, there is mentioned about a method which is suitable in a point that the protective film can be attached to a desired position after the place has been specified. By using an apparatus possessing an SEM which has been disposed so as to irradiate the same point as the FIB, after a position has been approximately specified by this SEM, the protective film of about 50 nm which is thicker than at least a penetration depth of the FIB is attached by an EB-CVD. In a case where a thicker film is necessary, the film may be additionally formed by the FIB-CVD by which a high-speed film-formation is possible. Subsequently, as shown in FIG. 1A, a boring working by an FIB etching is performed to a four-direction periphery of the observation-desired place, and it is cut off from the device by performing a bottom cut by means of FIB etching by tilting a sample stage such that the FIB irradiation is possible from a direction along which a large bore has been opened. As shown in FIG. 1B, a block-like observation sample piece (sample block) 1 having been cut off is carried onto a fixing substrate 2 by a fine probe 3 which is operated by a manipulator, and temporarily fixed by the FIB-CVD. Since the cut-out sample piece 1 at this time is bottom-cut by the FIB from a tilt angle direction, it follows that a bottom part has a slant angle with respect to the surface, so that a fixation to the sample fixing base 2 is performed so as to fill a slant portion as shown in the drawing. The above processes are ones conforming to a method disclosed in "Method of positioning a vertical position of a pickup sample and a sample having a mark showing a vertical direction" Specification (Patent Document 1) relating to a sample for transmission electron microscope, which was previously developed by a group of the present inventors and applied for as the Japanese Patent Application No. 2003-157120.

Figure 1C:
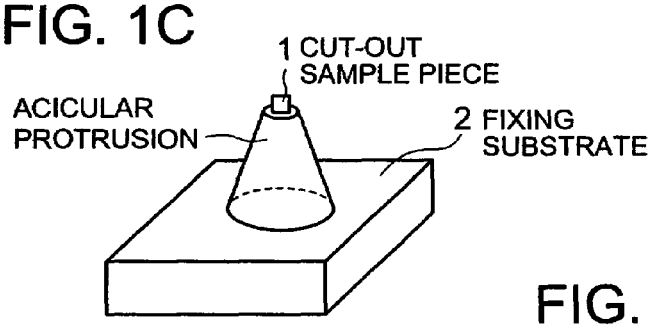
Figure 1D:
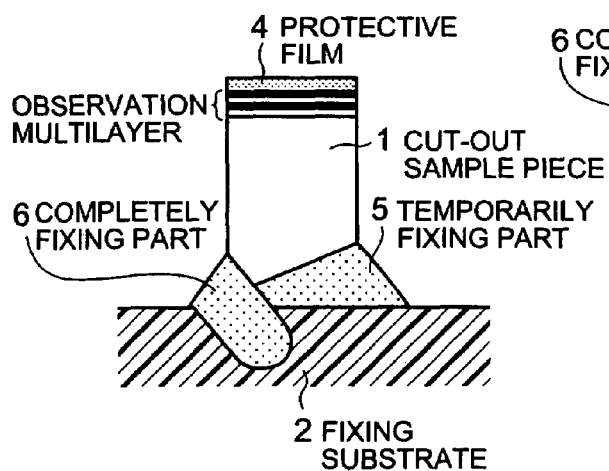
Figure 1E:
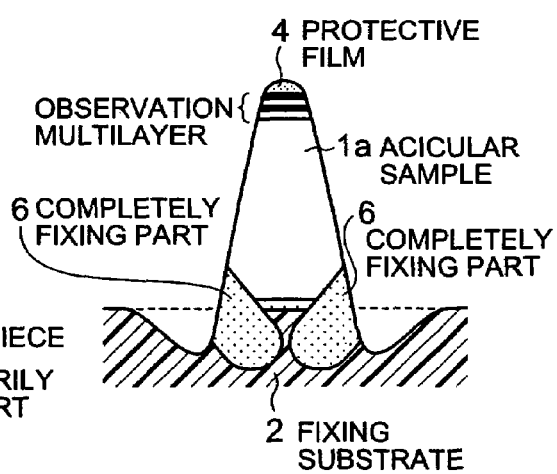

After the block-like sample piece 1 cut-out onto the fixing substrate by the FIB etching with the place that is desired to be analyzed being specified has been temporarily fixed (5 temporarily fixing-part), the sample stage is tilted and a groove is cut in over a base part of the block-like sample piece 1 and the fixing substrate 2 by the FIB etching. In addition to this, the FIB-CVD is applied to the cut-in portion, and thereby the sample substrate and the block-like sample are completely fixed by bonding (6 completely fixing part). This state is shown in FIG. 1D. By applying this complete fixation to plural places, the block-like sample piece 1 is firmly adhered to the fixing substrate 2. Finally, this block-like sample piece 1 is formation-worked into a needle shape by the FIB etching. An acicular sample 1a having been preliminarily worked in this manner is shown in FIG. 1E. Here, as shown in FIG. 1B, although the fixing substrate 2 was made a flat plate larger than the cut-out sample piece 1, depending on a case there may be worked such that, as shown in FIG. 1C, an acicular protrusion whose tip has been made flat is previously provided on the fixing substrate 2, and thereon the cut-out sample piece 1 is fixed, so that the whole becomes a large acicular form. This is because, in order to concentrate the electric field to a sample needle tip, it is necessary to make a length of the needle into several times of a diameter of the ion lead-out electrode. By previously providing the protrusion on the fixing substrate as mentioned above, it becomes possible to deal with even a case where the diameter of the ion lead-out electrode of the AP is large. If an acceleration voltage is made low, since a depth to which there exerts the damage occurring by the fact that the irradiation ions such as gallium are driven into the sample by the FIB working can be made shallow, a thickness of a damage layer can be made 10 nm or less if a finish working is performed by the acceleration voltage of 5-10 kV or lower. Since a tip diameter of the sample needle is about 200 nm, the analysis of a large portion region excluding one part of an outer periphery part becomes possible. Additionally, it is also effective to include a process of removing the damage layer by a low acceleration Ar ion milling and the like.

The sample having been worked in this manner becomes a form in which different materials have been laminated in multiple over a direction from the tip toward a base part of the needle. Although it follows that this sample is set to the SAP, a voltage is applied between the sample substrate and a hollow conical lead-out electrode, and an element analysis is performed by an ion detector by ion-evaporating every atom layer from a sample tip portion, it is a publicly known technical matter that, on that occasion, an electric field intensity necessary for the electric field evaporation greatly differs depending on the element. In the Non-Patent Document 2, values of the evaporation electric field, which is found from a theoretical expression, and an evaporation electric field experiment value are shown about each element in the Table.

For this reason, in the AP analysis of a multilayer thin film sample, for each layer it is necessary to rapidly switch an applied electric field intensity to a suitable value, thereby advancing the analysis. In such a case that a layer whose interface adhesion intensity is small exists below a layer of the element whose evaporation electric field is especially large, there occurs a problem that an adhesion force is defeated by an electrostatic attracting force to thereby cause an exfoliation in that weak interface, so that the sample above that layer flies off.

Whereupon, the present inventors have further developed an atom probe apparatus which, in the multilayer structure of the sample even if there exists the interface liable to be exfoliated, makes a stable ion evaporation possible without such a fact that the exfoliation occurs in a portion of the layer of that element, thereby making the analysis at the atomic level possible.

As one method of solving this problem, in a case where in the thin film sample there are layers whose evaporation electric fields are large and small with an interface whose adhesion intensity is small being nipped between them, the sample is bonded onto the sample substrate by cutting out a sample direction such that the layer whose evaporation electric field is small becomes a surface side. By disposing in this manner, the analysis at the atomic level becomes possible by adapting such that in the beginning the atom of the layer whose evaporation electric field is small is ion-evaporated by a low voltage application and, after that atom layer has evaporated, the atom of the layer whose evaporation electric field is large is ion-evaporated by intensifying the electric field.

Figure 2A:
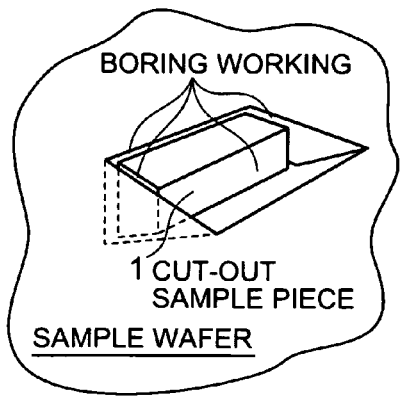
Figure 2B:
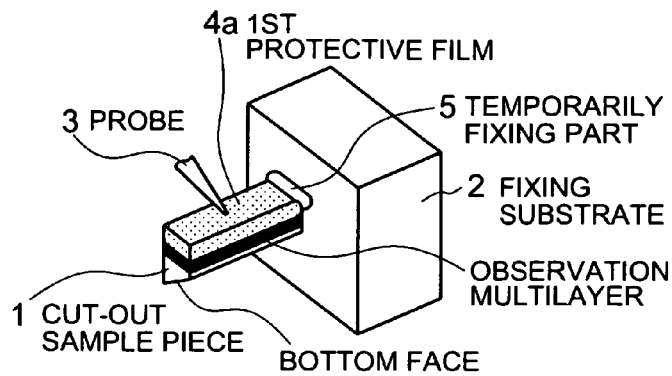
Figure 2C:
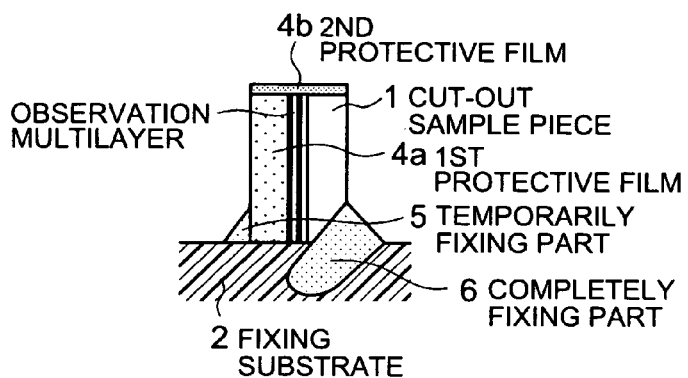

In a case where, in the multilayer thin film sample, a layer whose interface adhesion intensity is small exists in an intermediate layer, since this method cannot be adopted, in the present invention it has been thought of to work a sample structure such that a direction of the interface of each layer becomes a longitudinal direction of the sample needle. A preliminary working of the sample in this case is advanced in such a manner as shown in FIG. 2. As a finish of the sample working, a block cutting-out working by the FIB etching is performed such that a lamination layer comes a longitudinal direction of a needle shape. Generally, since a lamination structure of the semiconductor element becomes parallel in its layer face to the surface, although it follows that a rectangular area is shallowly cut out as shown in FIG. 2A, before it an analysis place is positioned and a 1st protective film 4a is previously formed in a surface of that region so as not to undergo the damage by the FIB. For this purpose, it is suitable to use the aforementioned method described in the 9th line onward in the paragraph [0009]. Next, the cut-out sample piece 1 containing an observation region is cut out by the FIB etching, it is carried onto the substrate 2 for fixing this cut-out sample piece 1 by the fine probe 3 by operating the manipulator as shown in FIG. 2B, and temporarily fixed (5 temporarily fixing part) by the FIB-CVD. At this time, since the direction of the sample piece 1 is one forming the needle shape, it follows that the sample piece is fixed with its longitudinal direction being made a direction perpendicular to the sample substrate 2. After the temporary fixation has been finished, although it follows that the complete fixation (6 completely fixing part) is applied, on that occasion as shown in FIG. 2C, a 2nd protective film 4b is formed in the sample tip part by the FIB-CVD in order to prevent the damage by the FIB irradiation. Before forming this protective film 4a, it is necessary that a position information of the multilayer structure portion becoming the observation region is previously detected by an SIM. In a method of completely fixing the block-like cut-out sample piece 1 onto the sample fixing substrate 2, the FIB is irradiated from obliquely above over the base part of the block-like sample piece 1 and the sample substrate 2 by tilting the sample stage, the groove is cut in by the FIB etching, and the CVD is applied to that grooved portion by irradiating the FIB thereto while jetting thereon a raw material gas such as phenanthrene from a gas gun, thereby bonding and fixing the sample substrate and the block-like sample. By applying the bonding working like this to plural places, the block sample is firmly adhered to the sample substrate.

Figure 2D:
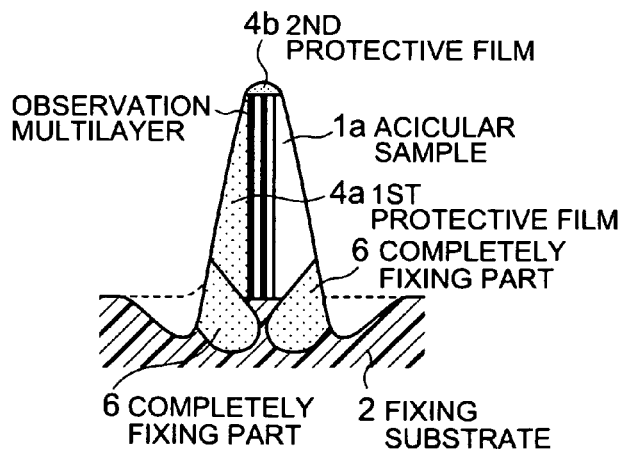

The columnar sample piece 1 having been fixed to the fixing substrate 2 is etched by performing thereto the FIB irradiation from above, thereby forming the needle shape. On this occasion, the etching working is applied on the basis of a position information in which there is previously detected and stored an information as to in which portion of the columnar sample piece 1 there is the observation region. A state having been worked in this manner is shown in FIG. 2D. A tip diameter is worked into about 0.2μmφ.

Figure 2E:
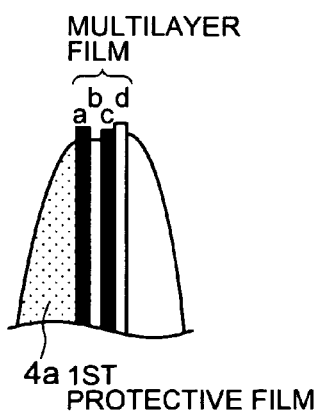
Figure 3:
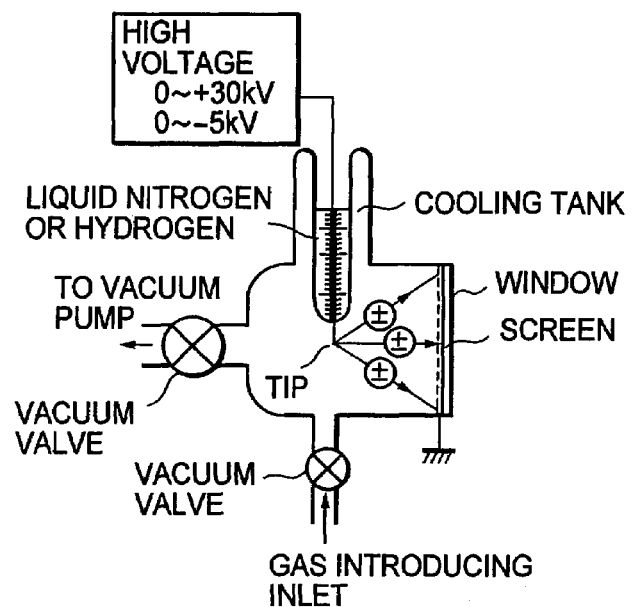
Figure 4:
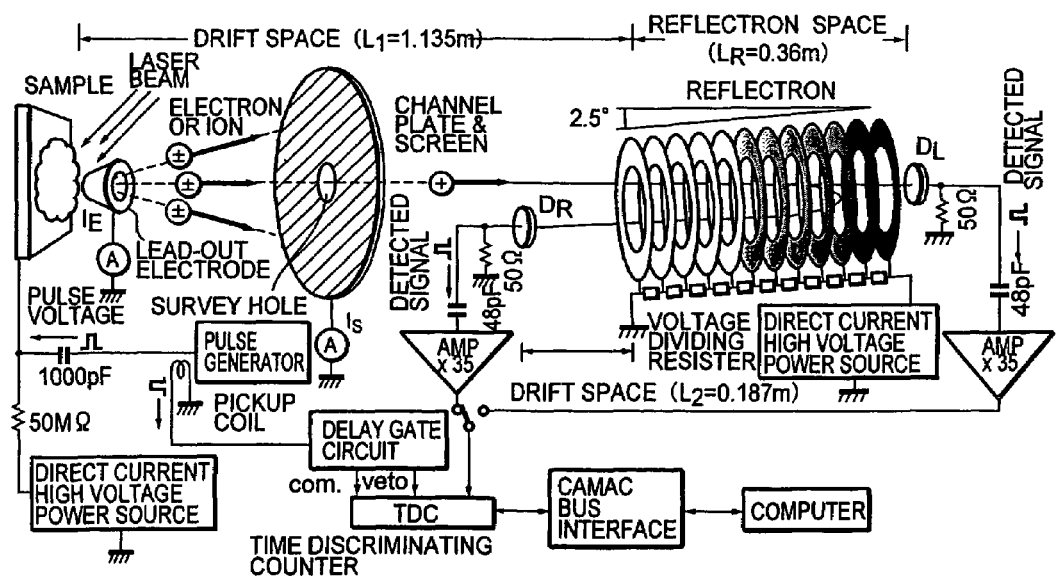

If the multilayer sample whose layer thickness extends to nm or sub-nano order is manufactured in the needle shape like this, since it follows that an end part of each layer is simultaneously exposed to a lead-out electric field, it follows that the atoms of each layer simultaneously begin an ionized evaporation. However, among others, the atom is first ionized and flies out from the layer of the element whose evaporation electric field is small. Then, since the layer whose evaporation electric field is relatively large is left, that layer becomes convex and the electric field is concentrated thereto, whereas the evaporated layer becomes concave, so that it follows that a step occurs in a position of the tip part as shown in FIG. 2E due to a difference in the evaporation electric field of the element. Although an end part of the layer whose evaporation electric field is low becomes low, if it becomes so, it follows that the electric field intensity formed between it and the lead-out electrode is decreased. As a result, if the applied voltage is constant, the ionization of the layer whose evaporation electric field is small slows down. Whereupon, if a lead-out electric field is set such that an ionization rate becomes constant in an analyzable range, it becomes balanced even if there is a deviation of time, and finally becomes such that all the layers are electric-field-evaporated. By this, it is possible to solve a disadvantage that the specified layer evaporates at high speed, and thus the analysis of each layer becomes impossible.

When analyzing this sample by the SAP, since there is a difference in a value of the evaporation electric field of each layer of a, b, c and d, if the electric field intensity is gradually increased, it is possible to first detect an element of the lowest value on the screen, and ones whose values of the evaporation electric field are low can be detected in order. If this is traced in time series, a corresponding relation can be taken even if a position of the tip part changes due to a difference in evaporation speed, so that a correction of the position is possible. That is, if the irregularities occur in an evaporation surface side, although it follows that a flying direction of the ion changes from a case of a simple needle tip, since there is obtained a correspondence between an ion generation place and an arrival position to the screen becoming the detector form a positional relation between the end part of each layer and the lead-out electrode, a position correction is possible. By these diverse analyses, there has become possible an atomic-level composition analysis of the multilayer structure sample of an ultra-thin dimension, which has been difficult hitherto.

The invention claimed is:

1. A method for working a sample preliminarily for an atom probe apparatus, comprising: a step of cutting out a desired sample observation part to a block-like form by using an FIB apparatus; a step of carrying and fixing the block-like cut-out sample onto a sample substrate; and a step of working the block-like sample fixed onto the sample substrate into a needle tip shape by an FIB etching, wherein the step of fixing the block-like cut-out sample onto the sample substrate includes a step of temporarily bonding it by an FIB-CVD, a step of cutting in a groove over a base part of the block-like sample and the sample substrate by an FIB etching, and a step of applying the FIB-CVD to the cut-in portion, thereby bonding and fixing the sample substrate and the block-like sample.

2. A method for working a sample preliminarily for an atom probe apparatus according to claim 1; wherein a finish working for working the block-like sample into the needle tip shape by the FIB etching is performed by an acceleration voltage of 10 kV or lower, thereby shallowing a damage layer.

3. A method for working a sample preliminarily for an atom probe apparatus according to claim 2; further comprising a step of additionally removing, after performing the finish working by the acceleration voltage of 10 kV or lower, the damage layer by a low acceleration Ar ion milling.

4. A sample for an atom probe apparatus, characterized in that the sample worked into a needle tip shape is formed such that a layer direction of a multilayer structure becomes parallel to a longitudinal direction of a needle.

5. A method of preparing a sample for an atom probe apparatus, comprising:
cutting out a sample block from a sample using a focused ion beam;
temporarily fixing a base part of the sample block to a substrate;
etching a groove in the base part of the temporarily fixed sample block and in the substrate using a focused ion beam;
completely fixing the sample block to the substrate by bonding using focused-ion-beam-assisted chemical vapor deposition applied to the groove; and
etching the completely fixed sample block into a needle shape using a focused ion beam.

6. A method according to claim 5; including etching plural grooves in the base part of the temporarily fixed sample block and in the substrate using a focused ion beam; and completely fixing the sample block to the substrate by bonding using focused-ion-beam-assisted chemical vapor deposition applied to the plural grooves.

7. A method according to claim 5; wherein the etching of the completely fixed sample block into a needle tip shape using a focused ion beam includes a finish working in which the etching is performed by the focused ion beam at an acceleration voltage of 10 kV or lower.

8. A method according to claim 7; further including removing a damage layer from the needle tip shape, caused by the focused ion beam etching, by ion milling.

9. A method according to claim 8; wherein the ion milling is carried out using Ar ions.

10. A method according to claim 5; wherein the temporarily fixing a base part of the sample block to a substrate is carried out by bonding using focused-ion-beam-assisted chemical vapor deposition.

11. A multilayer sample for an atom probe apparatus, in which the sample has a needle shape and a multilayer structure, and in which the layer direction of the multilayer structure is parallel to a longitudinal direction of the needle.

* * * * *